(12) United States Patent  
Urushidani

(10) Patent No.: US 8,988,683 B2  
(45) Date of Patent: Mar. 24, 2015

(54) FOOD ANALYSIS DEVICE

(71) Applicant: Seiko Epson Corporation, Tokyo (JP)

(72) Inventor: Tatsuo Urushidani, Chino (JP)

(73) Assignee: Seiko Epson Corportion, Tokyo (JP)

( * ) Notice: Subject to any disclaimer, the term of this patent is extended or adjusted under 35 U.S.C. 154(b) by 0 days.

(21) Appl. No.: 14/138,883

(22) Filed: Dec. 23, 2013

(65) Prior Publication Data

US 2014/0185046 A1 Jul. 3, 2014

(30) Foreign Application Priority Data

Dec. 27, 2012 (JP) ................................. 2012-284469

(51) Int. Cl.
  *G01J 3/46* (2006.01)
  *G01N 21/359* (2014.01)
(52) U.S. Cl.
  CPC ................................. *G01N 21/359* (2013.01)
  USPC ........................................................ 356/402
(58) Field of Classification Search
  CPC ................. G01J 3/46; G01J 3/50; G01J 3/02; G01J 3/524; G01J 3/51
  USPC ........................................................ 356/402
  See application file for complete search history.

(56) References Cited

U.S. PATENT DOCUMENTS

| 4,914,662 A * | 4/1990 | Nakatani et al. ................. 372/32 |
| 2007/0216898 A1* | 9/2007 | Gardner, Jr. .................... 356/301 |
| 2011/0299066 A1* | 12/2011 | Kusukame et al. ............. 356/51 |

FOREIGN PATENT DOCUMENTS

| JP | A-2004-354098 | 12/2004 |
| JP | A-2008-217702 | 9/2008 |

* cited by examiner

*Primary Examiner* — Tarifur Chowdhury  
*Assistant Examiner* — MD Rahman  
(74) *Attorney, Agent, or Firm* — Oliff PLC

(57) ABSTRACT

A food analysis device includes a variable wavelength interference filter adapted to disperse light reflected by the food into a plurality of lights with respective wavelengths, an imaging section adapted to image the lights with the respective wavelengths obtained by the dispersion to obtain spectral images corresponding respectively to the wavelengths, and a control section adapted to obtain spectrum of each of the pixels from the spectral images corresponding to the respective wavelengths, and then detect a pixel including the absorption spectrum of water, and then detect a plurality of components based on the spectrum of the pixel detected.

5 Claims, 6 Drawing Sheets

FOOD ANALYSIS DEVICE

BACKGROUND

1. Technical Field

The present invention relates to a food analysis device.

2. Related Art

In the past, there has been known a food analysis device for detecting a component (nutrient) included in a food (see, e.g., JP-A-2008-217702 (Document 1)).

The camera (the food analysis device) of Document 1 is provided with a flash memory storing a food dictionary having food characteristics data including shape patterns and color patterns representing shape characteristics of each food, and food data (food reference data) including component contents included in the food, the total calories of the food, and so on. Further, when a food is imaged by an imaging section, the food analysis device recognizes the type of the food based on the taken image and the food characteristics data, and then calculates an actual amount of the food based on the distance information obtained by a distance sensor or the like and a field angle of the camera, the shape of a serving dish, and so on. Then, the food analysis device calculates the component contents and the total calories of the food based on the food reference data of the food.

Incidentally, the food analysis device described above identifies the food based on the food characteristics data recorded in the food dictionary. Therefore, there is a problem that it is not achievable to identify the food not recorded in the food characteristics data. Further, in order to identify a larger number of foods, there arises a need for previously registering an extremely large amount of data, and a storage area with a large capacity also becomes necessary.

Further, the food analysis device described above calculates rough values of the component contents and the calorie of the food using the reference values of the component contents and the calorie recorded in the food reference data. However, since the component contents and the calorie per unit amount recorded in the food reference data are different from the component contents and the calorie per unit amount of the actual food, there is a problem that it is not achievable to calculate accurate component contents and calorie.

SUMMARY

An advantage of some aspects of the invention is to provide a food analysis device capable of appropriately detecting a food, and capable of accurately detecting the components included in the food.

A food analysis device according to an aspect of the invention is a food analysis device adapted to detect a plurality of components included in a food, including a spectroscopic element adapted to disperse light reflected by the food into a plurality of lights with respective wavelengths, an imaging element adapted to image the lights with the respective wavelengths obtained by the dispersion to obtain spectral images corresponding respectively to the wavelengths, and a processing section adapted to obtain a spectrum of each of pixels from the spectral images corresponding respectively to the wavelengths to detect the pixel including an absorption spectrum of water, and then detect the plurality of components.

In the aspect of the invention, the light reflected by the food is dispersed by the spectroscopic element into the lights with the respective wavelengths, and the lights thus dispersed are imaged by the imaging element. Here, the imaging element receives the lights by each of the pixels independently of each other to thereby obtain the spectral images (taken images) constituted by the plurality of pixels. Then, the processing section obtains the spectrum in the predetermined wavelength band for each of the pixels from the light intensity of each of the pixels of the spectral images corresponding to the respective wavelengths, and the pixel having the spectrum including the absorption spectrum of water is detected as the pixel corresponding to the food. Then, the processing section detects the components included in the food based on the spectrum of the pixel thus detected.

According to the aspect of the invention described above, the components included in the food can be detected pixel by pixel from the spectrum of each of the pixels. Therefore, by detecting the content amount of each of the components with respect to all of the pixels corresponding to the food, it becomes possible to accurately obtain the content amount of each of the components included in the food.

Further, in the aspect of the invention, by detecting the presence or absence of water, the pixels corresponding to the food in the spectral image are detected. The absorption spectrum of water has a plurality of optical absorption wavelengths (the peak wavelengths) in the near-infrared range, and shows the absorption property in a wide wavelength range at each of the peaks. Thus, the presence or absence of water can easily and accurately be detected from the dispersion spectrum. Specifically, in the case of detecting the pixels corresponding to the food using the component having the (peaked) peak wavelength in a narrow wavelength range, it is necessary to measure the light intensity corresponding to the peak wavelength in a pin-point manner, and the detection accuracy is degraded. In contrast, in the case of using the absorption spectrum of water as described above, by sequentially measuring the wavelength at regular intervals (e.g., 10 nm), the detection of water becomes possible, and therefore, the pixel corresponding to the food can easily and accurately be detected.

In the food analysis device according to the aspect of the invention, it is preferable that the spectroscopic element performs integral-field spectroscopy on the light reflected by the food, and the imaging element receives the light obtained by the integral-field spectroscopy using the spectroscopic element by each of the pixels independent of each other to obtain the spectral image constituted by the plurality of pixels.

Here, the integral-field spectroscopy described in the specification denotes an operation of dispersing the light included in a predetermined area in a light cross section perpendicular to the incident direction of the light in a lump.

In general, in the case of adopting a configuration of dispersing only the incident light having entered a predetermined point in the light entrance area in the spectroscopic element, there arises a necessity of translating the point capable of dispersing the incident light by, for example, translating the spectroscopic element to thereby individually detect the light intensity of each of the pixels in order to obtain the light intensity with respect to each of the pixels to thereby obtain the taken image. In contrast, in the configuration described above, by using the spectroscopic element capable of performing the integral-field spectroscopy, it is possible to disperse the incident light having entered the light entrance area in a lump. Therefore, also in the imaging element, by receiving the light thus dispersed pixel by pixel, the spectral image can easily be obtained.

In the food analysis device according to the aspect of the invention, it is preferable that the spectroscopic element is a variable wavelength Fabry-Perot etalon element.

The variable wavelength Fabry-Perot etalon element is an element having a pair of reflecting films disposed so as to be opposed to each other, and being capable of easily varying the spectroscopic wavelength by varying the gap dimension between these reflecting films. By using such a variable wavelength Fabry-Perot etalon element, miniaturization becomes possible compared to the food analysis device using a large-sized spectroscopic element such as an acousto-optic tunable filter (AOTF) or a liquid crystal tunable filter (LCTF).

Further, since the portability is also improved due to the miniaturization of the device, it is possible to easily detect the components of the food when, for example, eating out. Further, due to the improvement of the portability, it becomes also possible to change the posture of the food analysis device so that the food fits into the spectral image and the background pixels other than the food are reduced.

In the food analysis device according to the aspect of the invention, it is preferable that the processing section calculates calorie of the food based on the plurality of components detected.

In the configuration described above, the calorie of the food is calculated in addition to the detection of each of the components of the food. As described above, in the food analysis device according to the aspects of the invention, since the components of the food can accurately be detected, and the accurate content amount of each of the components can be obtained, the accurate calorie can be calculated based on these content amounts of the components.

BRIEF DESCRIPTION OF THE DRAWINGS

The invention will be described with reference to the accompanying drawings, wherein like numbers reference like elements.

DESCRIPTION OF AN EXEMPLARY EMBODIMENT

A food analysis device according to an embodiment of the invention will hereinafter be explained with reference to the accompanying drawings.

Schematic Configuration of Food Analysis Device

Figure 1:
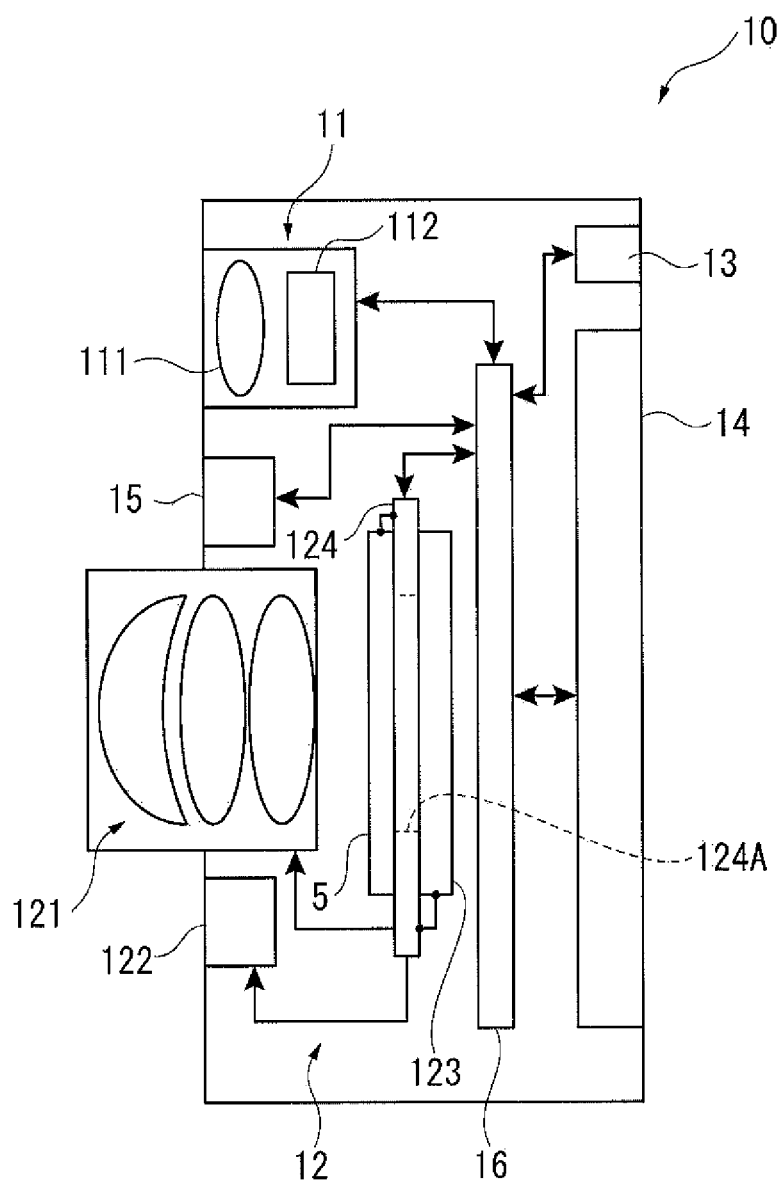
FIG. 1 is a diagram showing a schematic configuration of a food analysis device according to an embodiment of the invention.

FIG. 1 is a diagram showing a schematic configuration of the food analysis device according to the present embodiment.

As shown in FIG. 1, the food analysis device 10 is provided with a visible light imaging module 11, a near-infrared imaging module 12, an input section 13, a display section 14, a temperature sensor 15, and a control section 16. The food analysis device 10 takes spectral images of a food as a measurement target with respect to a plurality of wavelengths using the near-infrared imaging module 12, and then obtains a dispersion spectrum in each pixel based on the light intensity of the pixel of the spectral images. Further, the food analysis device 10 measures the content rates and contents of the components, and the calorie included in the food as the measurement target based on the dispersion spectrum of each of the pixels obtained. Hereinafter, each constituent of the food analysis device 10 will be explained in detail.

Configuration of Visible Light Imaging Module

The visible light imaging module 11 is provided with a visible light entrance section 111, and a color imaging section 112. It should be noted that although FIG. 1 shows an example of the visible light entrance section 111 formed of a single lens, in reality, the visible light entrance section 111 is composed of a plurality of lenses, and a virtual image of the measurement target food is imaged by these lenses on the color imaging section.

The color imaging section 112 is configured including an imaging element for taking a color image, and takes a color taken image of the incident light, and then outputs the color taken image to the control section 16.

Configuration of Near-Infrared Imaging Module

The near-infrared imaging module 12 is provided with a light entrance section 121, a light source section 122, a variable wavelength interference filter 5, an imaging section 123, and a module substrate 124.

Configuration of Light Entrance Section

Although not shown in the drawings, the light entrance section 121 is composed of a plurality of lenses, and forms a virtual image of the measurement target food within the view angle on the imaging section 123 via the variable wavelength interference filter 5. It is preferable to use telecentric lenses as these lenses, and by using the telecentric lenses, it is possible to align the optical axis of the incident light to a direction parallel to the principal ray, and it becomes possible to make the incident light perpendicularly enter a stationary reflecting film 54 and a movable reflecting film 55 of the variable wavelength interference filter 5 described later.

Configuration of Light Source Section

The light source section 122 is provided with a plurality of types of light sources different in emission wavelength from each other. Specifically, the light source section 122 is provided with a visible light source for emitting visible light, and a near-infrared light source for emitting near-infrared light. Further, the near-infrared light source can also be formed of a plurality of types of light sources different in emission wavelength from each other, and in this case, it is also possible to switch between the light sources in accordance with a componential analysis target under the control of the control section 16.

Configuration of Variable Wavelength Interference Filter

The variable wavelength interference filter 5 is a variable wavelength Fabry-Perot etalon element constituting the spectroscopic element in the invention.

Figure 2:
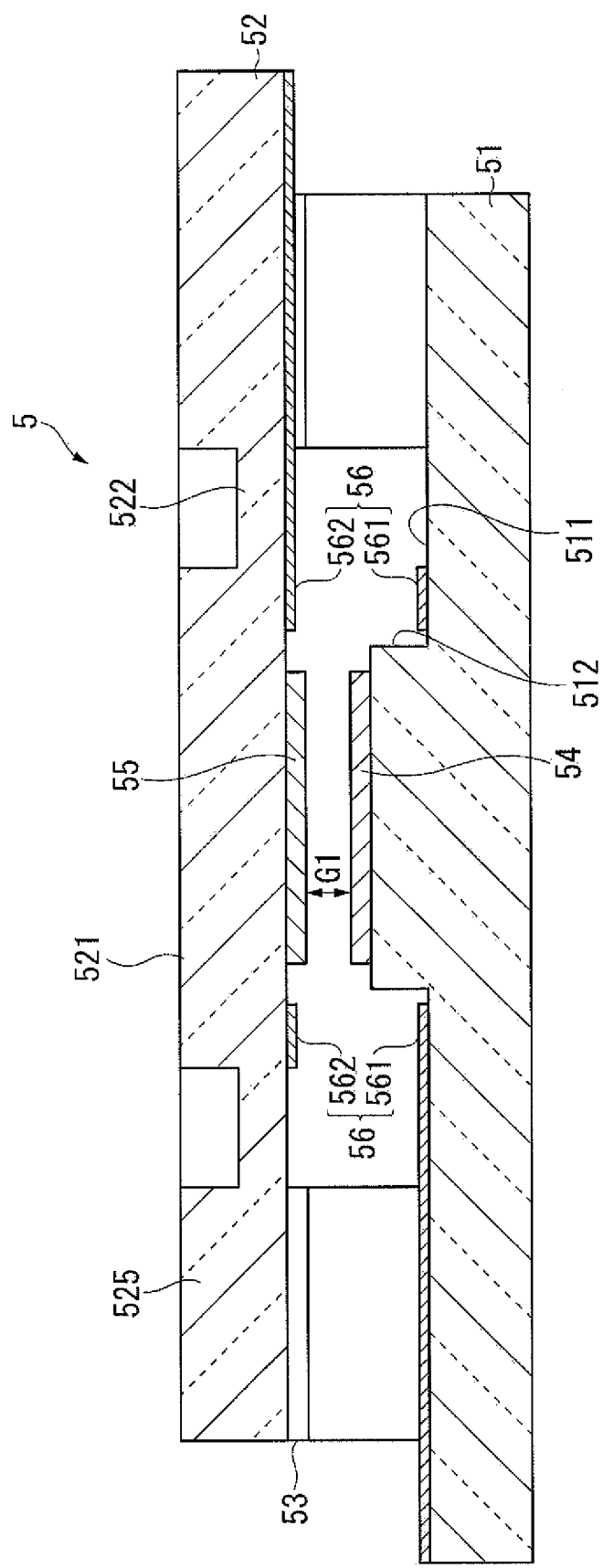
FIG. 2 is a cross-sectional view showing a schematic configuration of a variable wavelength interference filter according to the embodiment.

FIG. 2 is a cross-sectional view showing a schematic configuration of the variable wavelength interference filter 5.

The variable wavelength interference filter 5 is provided with a stationary substrate 51 formed to have a thickness dimension of, for example, about 500 μm, and a movable substrate 52 formed to have a thickness dimension of, for example, about 200 μm, and the stationary substrate 51 and the movable substrate 52 are bonded to each other with a bonding film 53 formed of, for example, a plasma polymerized film consisting mainly of siloxane to thereby be configured integrally. By using such a variable wavelength interference filter 5, miniaturization of the device can further be promoted compared to, for example, the case of using an AOTF or an LITF as the spectroscopic element, and thus a portable food analysis device 10 capable of calculating the calorie of a food can be configured.

The stationary substrate 51 is provided with an electrode arrangement groove 511 and a reflecting film installation section 512 formed by etching. Further, the electrode arrangement groove 511 is provided with a stationary electrode 561, and the reflecting film installation section 512 is provided with the stationary reflecting film 54.

The stationary electrode 561 is formed in the electrode arrangement groove 511 to have, for example, a ring-like shape surrounding the reflecting film installation section 512.

As the stationary reflecting film 54, a metal film made of, for example, Ag, or an alloy film made of, for example, an Ag alloy can be used. Further, it is also possible to use a dielectric multilayer film with a high refractive index layer made of, for example, $TiO_2$, and a low refractive index layer made of, for example, $SiO_2$. Further, it is also possible to use a reflecting film obtained by stacking a metal film (or an alloy film) on a dielectric multilayer film, a reflecting film obtained by stacking a dielectric multilayer film on a metal film (or an alloy film), a reflecting film obtained by laminating a single refractive layer (made of, e.g., $TiO_2$ or $SiO_2$) and a metal film (or an alloy film) with each other, and so on.

As shown in FIG. 2, the movable substrate 52 is provided with a movable section 521, and a holding section 522 disposed outside the movable section 521, and for holding the movable section 521.

The movable section 521 is formed to have a thickness dimension larger than that of the holding section 522, and is formed in the present embodiment, for example, to have the same thickness dimension as that of the movable substrate 52. The movable section 521 is formed to have a diameter larger than at least the diameter of the outer peripheral edge of the reflecting film installation section 512 in a filter plan view. Further, the movable section 521 is provided with a movable electrode 562 and the movable reflecting film 55.

The movable electrode 562 is disposed at a position opposed to the stationary electrode 561. Further, the movable reflecting film 55 is disposed at a position opposed to the stationary reflecting film 54 via an inter-reflecting film gap G1. As the movable reflecting film 55, a reflecting film having the same configuration as that of the stationary reflecting film 54 described above is used.

The holding section 522 is a diaphragm surrounding the periphery of the movable section 521, and is formed to have a thickness dimension smaller than that of the movable section 521. Such a holding section 522 is easier to be deflected than the movable section 521, and it becomes possible to displace the movable section 521 toward the stationary substrate 51 with a weak electrostatic attractive force. Thus, it becomes possible to vary the gap dimension of the inter-reflecting film gap G1 in the state of keeping the parallelism between the stationary reflecting film 54 and the movable reflecting film 55.

It should be noted that although in the present embodiment the holding section 522 having a diaphragm shape is shown as an example, the shape is not limited thereto, but a configuration of, for example, providing beam-like holding sections arranged at regular angular intervals centered on the planar center point can also be adopted.

In such a variable wavelength interference filter 5 as described above, the stationary electrode 561 and the movable electrode 562 constitute an electrostatic actuator 56, and these electrodes 561, 562 are connected to the control section 16 via the module substrate 124 (a driver). Further, under the control of the control section 16, a voltage control circuit applies a voltage to the electrostatic actuator 56 to thereby exert the electrostatic attractive force corresponding to the voltage between the electrodes 561, 562, and thus the gap dimension of the inter-reflecting film gap G1 is varied. Thus, it becomes possible to change the wavelength of the light to be transmitted through the variable wavelength interference filter 5.

Configuration of Imaging Section

Going back to FIG. 1, the imaging section 123 corresponds to the imaging element according to the invention, and receives the near-infrared light transmitted through the variable wavelength interference filter 5, and then outputs an image signal based on the taken image (the spectral image). As such an imaging section 123, an image sensor such as a CCD sensor or a CMOS sensor can be used. Further, in the present embodiment, since the visible light imaging module 11 takes a color image, it is sufficient for the imaging section 123 to be capable of taking a monochrome image with a predetermined wavelength in the infrared range, and therefore, the imaging element for taking a monochrome image can be used as the imaging section 123. In this case, it is possible to dispose one imaging element to one pixel, and thus, compared to the imaging section for taking a color image, which is required to dispose, for example, the imaging elements corresponding to R, G, and B to one pixel, a light receiving surface per pixel can be enlarged, and the light with the target wavelength can more efficiently be received. Thus, the received light intensity sufficient for the componential analysis can be ensured, and the analytical precision can be improved.

It should be noted that in the configuration having a near-infrared high-pass filter disposed in a light path, an image sensor having a sensitivity characteristic in a wide range from the near-infrared range to the visible light range (or the ultraviolet range) can be used as the imaging section 123. In contrast, in the configuration having no near-infrared high-pass filter disposed, in order to prevent the light in the visible light range or the ultraviolet range transmitted as a second-order peak or a third-order peak from the variable wavelength interference filter from being received, it is possible to use the imaging element such as a GaAs photosensor having a sensitivity characteristic low with respect to the range from the ultraviolet range to the visible light range and high with respect to the near-infrared range.

Then, the imaging section 123 outputs the image signal of the spectral image to the control section 16.

Further, in the present embodiment, the variable wavelength interference filter 5 as the variable wavelength Fabry-Perot etalon element is used as the spectroscopic element. In such a variable wavelength interference filter 5, so-called integral-field spectroscopy for dispersing the light having entered the optical interference region in a lump becomes possible, wherein the stationary reflecting film 54 and the movable reflecting film 55 are opposed to each other in the optical interference region. Therefore, by receiving the light, on which the integral-field spectroscopy has been performed, by the imaging section 123 pixel by pixel, the spectral image corresponding to one wavelength can be obtained at one imaging process.

Configuration of Module Substrate

The module substrate 124 is provided with the light source section 122, the imaging section 123, and the driver (the control circuit) for performing the drive control on the variable wavelength interference filter 5, and controls each constituent of the near-infrared imaging module in response to an instruction from the control section 16.

In the present embodiment, the variable wavelength interference filter 5 and the imaging section 123 are disposed across the module substrate 124, and are fixed to the module substrate 124. The light having been transmitted through the variable wavelength interference filter 5 passes through a light passage hole 124A provided to the module substrate 124, and is then received by the imaging section 123. In such a configuration as described above, it becomes possible to dispose the variable wavelength interference filter 5 and the imaging section 123 close to each other, and thus, miniaturization and height reduction of the food analysis device 10 can be achieved.

It should be noted that in the present embodiment, since the color image is taken by the visible light imaging module 11, it is sufficient for the near-infrared imaging module 12 to take the spectral image in the near-infrared range. Therefore, a near-infrared high-pass filter for transmitting only the light with a wavelength in the near-infrared range can also be provided in order to block, for example, the visible light (and the ultraviolet light) transmitted as the second-or-higher-order peak wavelength in the light transmitted through the variable wavelength interference filter 5. Such a near-infrared high-pass filter can be disposed at any position on the light path of the incident light in the infrared imaging module 12, and positions, for example, between the imaging section 123 and the variable wavelength interference filter 5, between the light entrance section 121 and the variable wavelength interference filter 5, and between the lenses of the light entrance section 121 can be cited.

Configuration of Input Section, Display Section, and Temperature Sensor

The input section 13 is constituted by, for example, an input button, a keyboard, a mouse, and a touch panel provided to the display section, and receives an operation by the user. Further, the input section 13 inputs an operation signal based on the operation by the user to the control section 16.

The display section 14 is formed of, for example, a display device such as a liquid crystal panel, and displays an image based on the image signal input from the control section 16.

The temperature sensor 15 detects the temperature of a test object. As the temperature sensor 15, for example, a thermopile array or a noncontact bolometer can be used.

Configuration of Control Section

Figure 3:
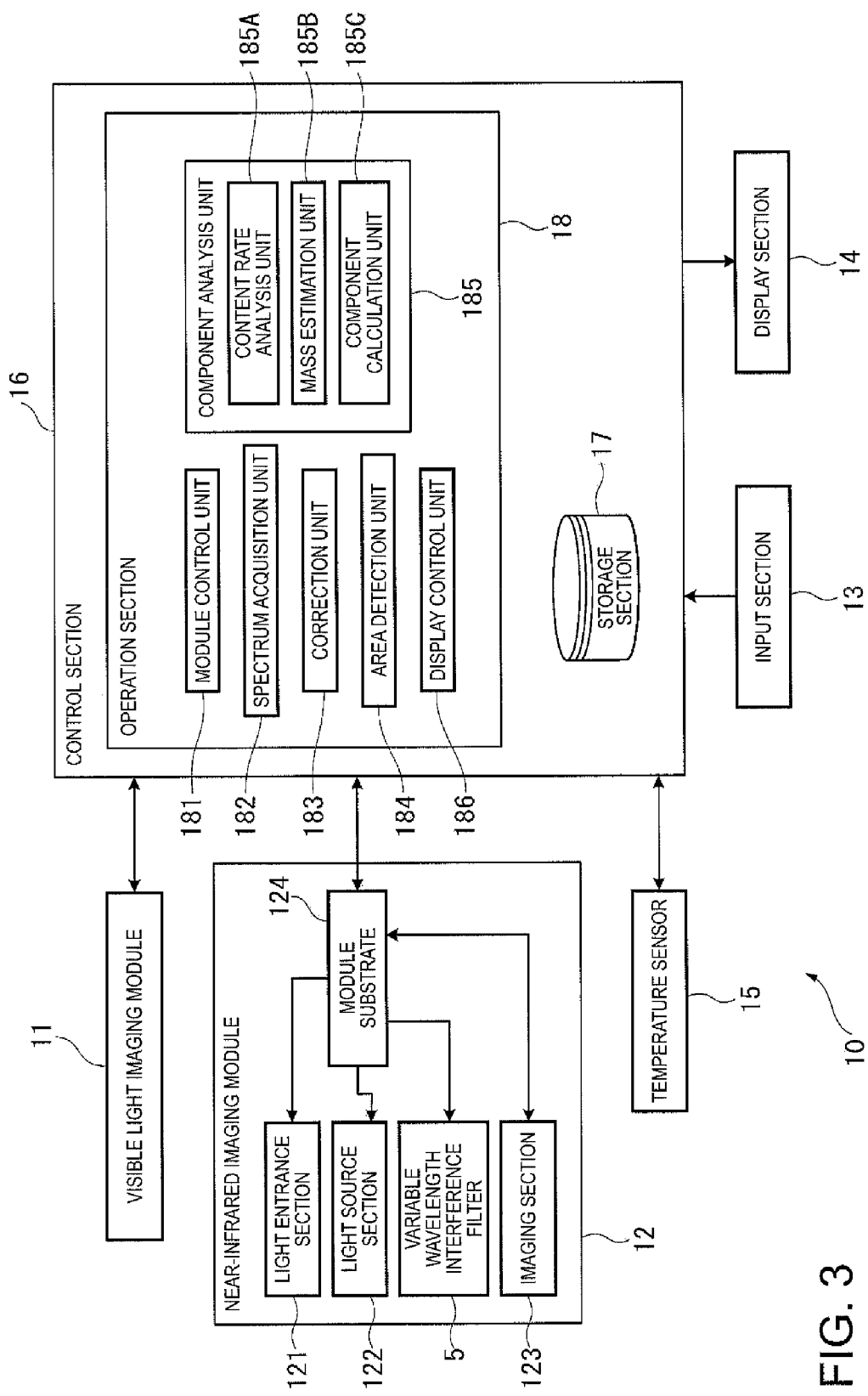
FIG. 3 is a block diagram showing a schematic configuration of the food analysis device according to the embodiment.

FIG. 3 is a block diagram showing a schematic configuration of the food analysis device according to the present embodiment.

The control section 16 is provided with a storage section 17 and an operation section 18.

The storage section 17 is constituted by, for example, a memory and a hard disk drive. The storage section 17 stores an operating system (OS), a variety of programs, a variety of data for controlling the overall operation of the food analysis device 10.

Further, the storage section 17 stores V-λ data for driving the electrostatic actuator 56 of the variable wavelength interference filter 5, and so on as the data described above.

Further, the storage section 17 stores correlation data (e.g., a calibration curve) representing the correlation between a feature quantity (absorbance at a specific wavelength) extracted from the absorption spectrum with respect to each component of the nutrient to be the analysis target, and the component content rate.

Further, the storage section 17 stores a correction value of the absorption spectrum of each component with respect to the temperature.

The operation section 18 is formed of an operational circuit such as a central processing unit (CPU), and a storage circuit. The control section 16 reads in a variety of programs stored in the storage section 17, and then executes the programs to thereby function as a module control unit 181, a spectrum acquisition unit 182, a correction unit 183, an area detection unit 184, a component analysis unit 185, and a display control unit 186 as shown in FIG. 3.

The module control unit 181 controls the visible light imaging module 11 and the near-infrared imaging module 12. In other words, the module control unit 181 controls the visible light imaging module 11 to obtain the color taken image.

Further, the module control unit 181 controls the near-infrared imaging module 12 to thereby control the electrostatic actuator 56 based on the v-λ, data stored in the storage section 17 to obtain the spectral images at predetermined wavelength intervals.

The spectrum acquisition unit 182 obtains the dispersion spectrum in each pixel of the spectral image based on the spectral image with respect to each wavelength obtained by the near-infrared imaging module 12.

The correction unit 183 detects the temperature of the food of the measurement target detected by the temperature sensor 15 to correct the absorption spectrum for determining each component.

The area detection unit 184 determines the pixel area corresponding to the food in the pixels of the taken image based on the dispersion spectrum of each of the pixels.

The component analysis unit 185 is provided with a content rate analysis unit 185A, a mass estimation unit 185B, and a component calculation unit 185C.

The content rate analysis unit 185A analyzes the components included in the food based on the dispersion spectrum of each of the pixels, and analyzes the content rate of each of the components.

The mass estimation unit 185B estimates the volume of the food of the measurement target based on the taken image, and then estimates the mass based on the volume thus estimated. It should be noted that although in the present embodiment, an example of estimating the mass using the mass estimation unit 185B is described, it is also possible to adopt a configuration in which, for example, a digital balance or the like is provided to a part of the food analysis device 10, and the mass measured by the digital balance is obtained.

The component calculation unit 185C calculates the content amount of each component included in the food, and the calorie of the food.

The display control unit 186 controls the display section 14 to make the display section 14 display the color image taken by the visible light imaging module 11, the spectral image taken by the near-infrared imaging module 12, an analysis result of the component analysis unit 185, and other variety of types of display images.

It should be noted that the detailed processing content of each constituent of the operation section 18 will be described later.

Component Analysis Process of Food by Food Analysis Device 10

Then, such a component analysis process by the food analysis device 10 as described above will hereinafter be explained with reference to the drawings.

Figure 4:
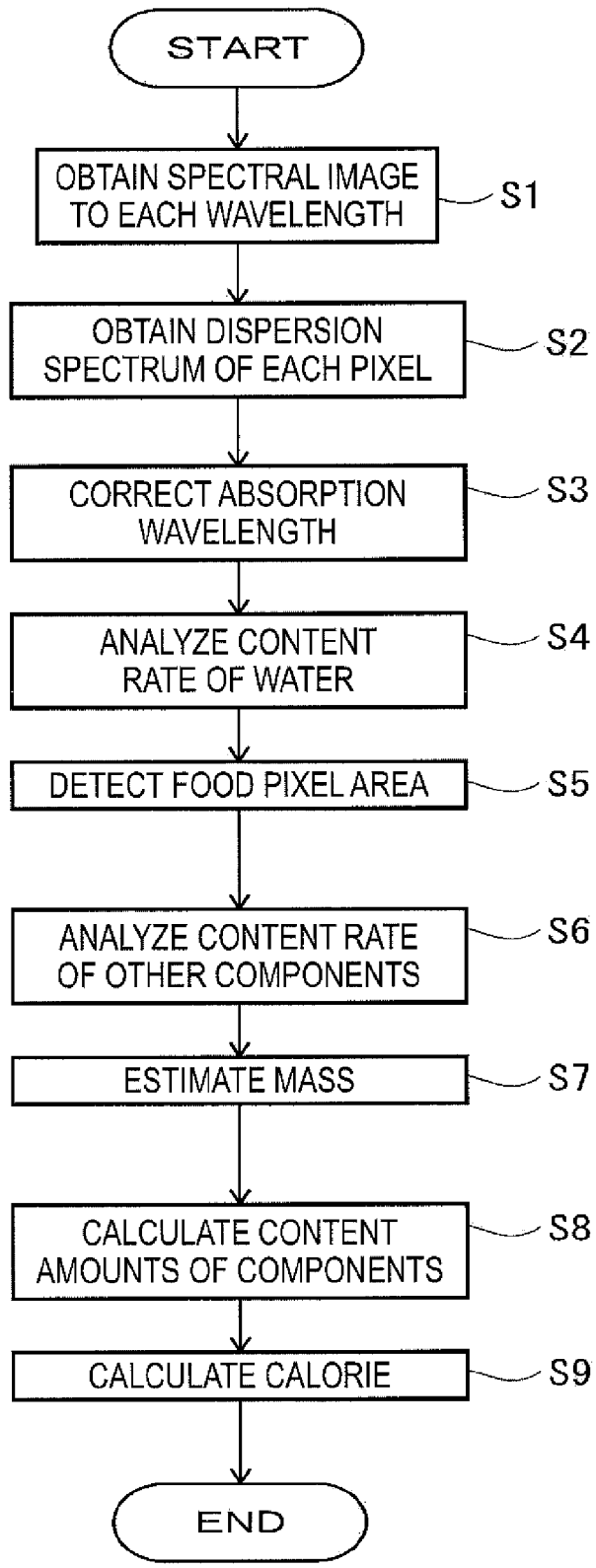
FIG. 4 is a flowchart showing a component analysis process using the food analysis device according to the embodiment.

FIG. 4 is a flowchart of the component analysis process performed by the food analysis device 10.

In the present embodiment, when the user sets the food of the measurement target at a predetermined position, and then the near-infrared imaging module 12 images the food thus set in response to the operation of the user, the component analysis process on the food is performed.

To this end, as shown in FIG. 4, the module control unit 181 first reads in the V-λ data from the storage section 17, and then sequentially switches the voltage to be applied to the electrostatic actuator 56 of the variable wavelength interference filter 5 to thereby switch the wavelength of the light to be transmitted through the variable wavelength interference filter 5 at predetermined intervals (e.g., 10 nm). Further, the module control unit 181 drives the imaging section 123 to image the light with each of the wavelengths transmitted through the variable wavelength interference filter 5. Thus, the spectral image corresponding to each of the wavelengths of the food of the measurement target can be obtained (step S1).

Figure 5:
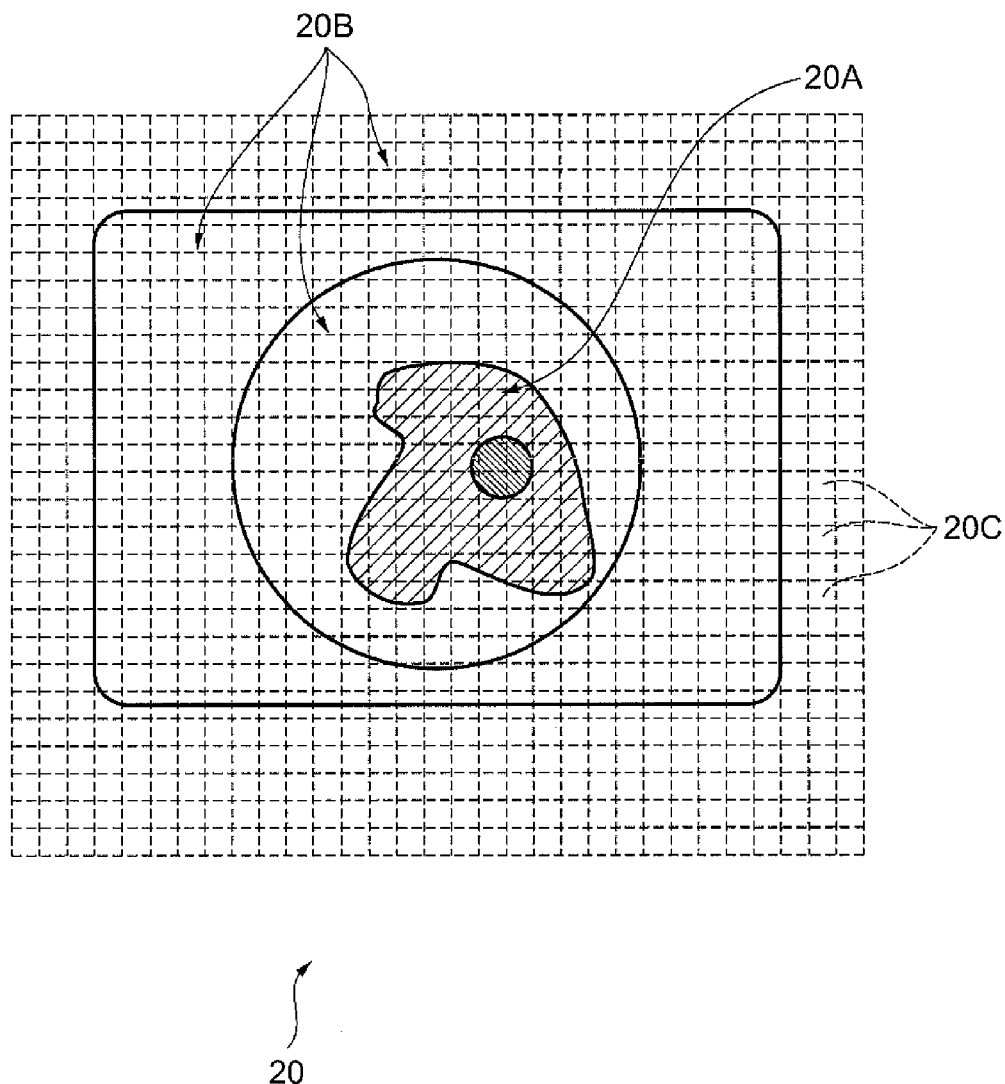
FIG. 5 is a diagram showing an example of a spectral image taken in the embodiment.

FIG. 5 is a diagram showing an example of the spectral image taken in the present embodiment.

When the food analysis device 10 obtains the spectral image in the step S1, the spectral image 20 including a food pixel area 20A corresponding to the food and a background pixel area 20B corresponding to an object other than the food such as a dish or a table can be obtained as in the example shown in FIG. 5.

Subsequently, the spectrum acquisition unit 182 obtains (step S2) the dispersion spectrum in each of the pixels 20C of the spectral image 20. Specifically, the spectrum acquisition unit 182 obtains the light intensity of each of the pixels of each of the spectral images taken at predetermined wavelength intervals (e.g., intervals of 10 nm), and obtains the dispersion spectrum in each of the pixels.

Then, the correction unit 183 detects the temperature of each of points of the food corresponding respectively to the pixels 20C from the temperature distribution of the food of the measurement target detected by the temperature sensor 15, and then corrects (step S3) the wavelength (the optical absorption wavelength) at which the feature quantity in each of the components can be obtained. Here, each of the components corresponds to the component to be the target on which the food analysis device 10 performs the analysis, and for example, water, glucide, lipid, and protein can be cited.

Specifically, the correction unit 183 multiplies the absorption spectrum of each of the components by the correction value of the correction data stored in the storage section 17.

For example, in the case in which the absorbance of the wavelength $\lambda_{A0}$ varies by the content rate of the component A at the reference temperature $T_0$, the feature quantity of the component A at the reference temperature $T_0$ becomes the absorbance of the wavelength $\lambda_{A0}$. However, there is a case in which the absorbance of the wavelength $\lambda_{A1}$ varies by the content rate of the component A at the temperature $T_1$, and in this case, the feature quantity of the component A at the temperature $T_1$ becomes the absorbance of the wavelength $\lambda_{A1}$. In particular, it is known that water significantly varies in absorption spectrum by the temperature variation, and the wavelength at which the feature quantity is detected needs to be corrected for performing the analysis of each of the components.

The correction unit 183 in the present embodiment reads out the correction value with respect to each temperature value of each of the components stored in the storage section 17, and then multiplies the wavelength $\lambda_{A0}$ by the correction value to thereby calculate the wavelength $\lambda_{A1}$ at which the feature quantity is detected with respect to the temperature $T_1$.

Then, the content rate analysis unit 185A of the component analysis unit 185 calculates (step S4) the content rate of water of the measurement target corresponding to each of the pixels based on the dispersion spectrum with respect to each of the pixels obtained in step S2.

More specifically, the content rate analysis unit 185A obtains the light intensity $I_{\lambda aq}$ with respect to the absorption spectrum wavelength $\lambda aq$ of water in each of the pixels, and then calculates the absorbance $A_{\lambda aq}$ based on Formula (1) below. It should be noted that $I_0$ denotes a basic received light intensity, which can be obtained when performing a calibration, and can be obtained by previously measuring the light intensity with respect to each of the wavelengths with respect to a reference object such as a white plate using, for example, the near-infrared imaging module 12.

$$A_{\lambda aq} = -\log(I_{\lambda aq}/I_0) \tag{1}$$

Then, the content rate analysis unit 185A analyzes the content rate of water based on absorbance $A_{\lambda aq}$ thus calculated, and the correlation data stored in the storage section 17. As the analysis method of the content rate of water described above, a chemometric method used previously can be cited. As the chemometric method, there can be used a method such as multi-regression analysis, principal component regression analysis, a partial least square method. It should be noted that since each of the analysis methods using these chemometric methods are techniques used previously, and the explanation thereof will be omitted here.

Subsequently, the area detection unit 184 detects (step S5) the pixels at which the content rate of water thus calculated in the step S4 becomes equal to or higher than a predetermined threshold value as the food pixel area 20A. In general, the component constituting a food includes much water, and in contrast, the region for mounting the food such as a dish, a table, or a cast-iron pan is small in content amount of water. Therefore, by assuming that the pixels at which the water content rate calculated with respect to each of the pixels becomes equal to or higher than the threshold value as described above are the constituent pixels of the food pixel area 20A, and the pixels at which the water content rate becomes lower than the threshold value are the constituent pixels of the background pixel area as described above, the food part and the background part in the spectral image can be separated from each other.

Further, in the separation between the food pixel area 20A and the background pixel area 20B based on the content rate of water, the pixel areas can be separated from each other more accurately than in the case of using other components.

Figure 6:
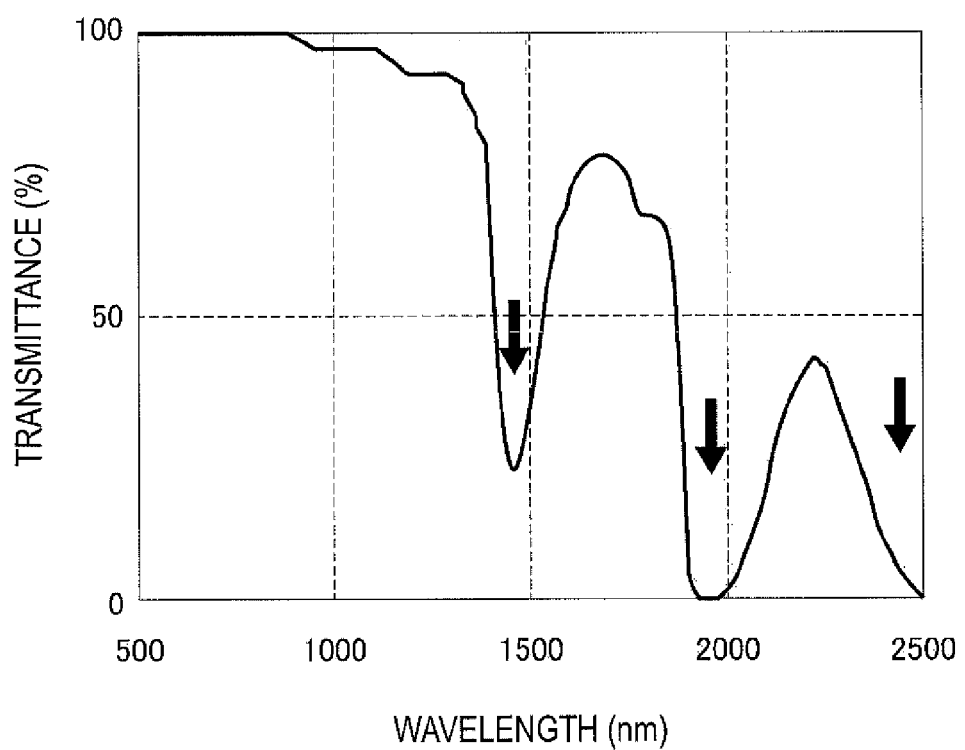
FIG. 6 is a diagram showing an optical absorption spectrum of water.

FIG. 6 is a diagram showing the absorption spectrum of water. As shown in FIG. 6, water has a broad optical absorption property in relatively wide wavelength range (e.g., 100 nm through 300 nm) in each of the vicinity of 1500 nm, the vicinity of 2000 nm, and the vicinity of 2500 nm. Therefore, the presence or absence of the component can more accurately be detected compared to the case of detecting the food pixel area 20A based on, for example, the component having a peaked optical absorption property in a narrow range centered on a predetermined absorption wavelength.

Subsequently, the content rate analysis unit 185A analyzes (step S6) the component content rate of other components (e.g., glucide, lipid, and protein) constituting the food based on the dispersion spectrum in each of the pixels in the food pixel area 20A.

Similarly to the step S4, in the step S6, the content rate analysis unit 185A calculates the absorbance $A_\lambda$ based on the light intensity $I_\lambda$ with respect to the absorption spectrum wavelength $\lambda$ of each of the components, and then analyzes the content rate of each of the components based on the absorbance $A_\lambda$ thus calculated and the correlation data.

It should be noted that it is also possible to analyze the content rate of other components at the same time when analyzing the content rate of water in the step S4.

Then, the content rate analysis unit 185A calculates an average value of the content rate in the pixels 20C in the food pixel area 20A with respect to each of the components, and defines the average value as the component content rate in the whole of the food. It should be noted that the component content rate of the whole of the food can also be obtained by picking up a plurality of pixels 20C from the food pixel area 20A thus detected, and then averaging the component content rate obtained by the analysis to these pixels 20C.

Then, the mass estimation unit 185B estimates (step S7) the mass of the food of the measurement target.

The mass estimation unit 183B first estimates the volume of the food based on the taken image. As the taken image, it is possible to use one of the spectral images obtained, or to use the color image which is in process of imaging.

In the present embodiment, it is preferable that the food of the measurement target is imaged in the state of being mounted on a dish (a reference material) having a known size. In this case, the mass estimation unit 185B estimates the rough volume of the test object by comparing the size of the dish and the size of the food with each other based on the taken image. It should be noted that it is also possible to perform the process of estimating the volume by imaging, for example, a scale or a marker as the reference substance besides the dish together with the food.

Further, the process is not limited to the estimation of the volume using the reference substance, but it is also possible to estimate the volume of the test object by, for example, image processing. For example, it is also possible to perform a process of obtaining the volume of the test object by three-dimensional analysis processing using the taken images obtained by imaging the test object from respective angles different from each other.

Then, the mass estimation unit 1853 estimates the mass of the food based on the content rate of each of the components thus analyzed in the steps of S4 and S6, and the volume thus estimated.

It should be noted that as the measurement of the mass of the food, it is also possible to perform a process of obtaining the mass input by the operation of the input section 13 by the user, besides the configuration of estimating the mass based on the taken images described above. Further, it is also possible to adopt a configuration of providing a mass measurement unit such as a digital balance to the food analysis device 10. In this case, it is possible to obtain the accurate mass measured by the mass measurement unit.

Subsequently, the component calculation unit 185C calculates (step S8) the content amount of each of the components based on the mass estimated in the step S7 and the content rate of each of the components analyzed in the step S6.

Further, the component calculation unit 185C calculates the calorie of the food from the content amounts of glucide, lipid, and protein thus calculated based on Formula (2).

$$\text{calorie (kcal)} = \text{lipid amount (g)} \times 9 + \text{protein amount (g)} \times 4 + \text{glucide amount (g)} \times 4 \quad (2)$$

Subsequently, the display control unit 186 makes the display section 14 display the component analysis result (the content rate and the content amount, and the calorie of each of the components) of the food.

Functions and Advantages of Present Embodiment

In the food analysis device 10 according to the present embodiment, the near-infrared imaging module 12 takes the spectral image of each of the wavelengths of the food of the measurement target, and the spectrum acquisition unit 182 obtains the dispersion spectrum in each of the pixels 20C based on the light intensity of each of the pixels 20C of the spectral image 20 thereof. Further, the area detection unit 184 detects the pixels 20C including the absorption spectrum of water as the food pixel area 20A to thereby separate the pixels from the other pixels, namely the background pixel area 20B. Then, the component analysis unit 185 calculates the content amount and the calorie of each of the components based on the dispersion spectrum of each of the pixels 20C in the food pixel area 20A.

As described above, in the present embodiment, by separating the food pixel area 20A and the background pixel area 20B from each other, the content amounts of the components included in the food can be detected based on the dispersion spectrum by pixel of the food pixel area 20A. Therefore, the total content amount of each of the contents included in the food can accurately be calculated.

Further, the food pixel area 20A and the background pixel area 20B are separated from each other based on whether or not the absorption spectrum of water is included. Since the absorption spectrum of water has a plurality of peaks in the near-infrared range, and these peaks each appear in a relatively wide range, the presence or absence of water can easily and accurately be detected in the dispersion spectrum of each of the pixels. Therefore, the food pixel area 20A and the background pixels area 20B can be separated from each other with high accuracy, and the area corresponding to the food in the spectral image can accurately be detected.

Further, in the present embodiment, there is provided the temperature sensor 15 for measuring the temperature distribution of the food, and the absorption spectrum of water is corrected based on the temperature distribution. In general, the absorption spectrum of water easily varies due to an influence of the temperature. In contrast, in the present embodiment, since the absorption spectrum can appropriately be corrected even in the case in which such a temperature variation exists, the presence or absence of water can be detected with accuracy, and the food pixel area 20A and the background pixel area 20B can be separated from each other with high accuracy.

In the present embodiment, the variable wavelength interference filter 5 as the variable wavelength Fabry-Perot etalon element is used as the spectroscopic element. The variable wavelength interference filter 5 has the stationary substrate 51 provided with the stationary reflecting film 54 and the movable substrate 52 provided with the movable reflecting film 55 opposed to each other, and varies the gap dimension between the reflecting films using the electrostatic actuator 56 to thereby transmit the light with the wavelength corresponding to the gap dimension. In such a variable wavelength interference filter 5, the substrates 51, 52 can be formed to have a thickness in a range of, for example, about 1 through 2 mm, and therefore, the variable wavelength interference filter is suitable for miniaturization and height reduction. Therefore, by using the variable wavelength interference filter 5 as the spectroscopic element, the miniaturization and height reduction of the food analysis device 10 can be achieved compared to the case of using the spectroscopic element formed of, for example, an AOTF or an LCTF.

Further, in such a variable wavelength interference filter 5, so-called integral-field spectroscopy for dispersing the light having entered the light interference region in a lump becomes possible, wherein the stationary reflecting film 54 and the movable reflecting film 55 are opposed to each other in the optical interference region. Therefore, the spectral image with respect to each of the wavelengths can promptly and easily be obtained compared to the case of using, for example, a filter for performing the spectroscopic process on a predetermined point in an optical interference region.

In the present embodiment, the calorie of the food is calculated in addition to the content amount of each of the components included in the food. As described above, in the present embodiment, the food pixel area 20A in the spectral image can accurately be detected, and at the same time, the accurate content amounts of the components of the food can be calculated based on the dispersion spectrum of each of the pixels 20C in the food pixel area 20A. Therefore, it is possible to calculate the accurate calorie based on such content amounts of the components. Thus, the health management of the user based on the correct calorie can be promoted.

Other Embodiments

It should be noted that the invention is not limited to the embodiment described above, but includes modifications, improvements, and so on within a range where the advantages of the invention can be achieved.

For example, although in the embodiment described above, there is described the configuration in which the variable wavelength interference filter 5 is fixed to the module substrate 124, the invention is not limited to this configuration, but it is also possible to adopt a configuration in which, for example, the variable wavelength interference filter 5 is housed in a package, and the package is fixed to the module substrate 124. Further, the variable wavelength interference filter 5 can also be fixed to a substrate other than the module substrate 124, or a fixation section provided to a device housing.

In the embodiment described above, there is described the example in which the food analysis device 10 is provided with the visible light imaging module 11, and the color image is taken by the visible light imaging module 11. In contrast, it is also possible to adopt a configuration in which the visible light imaging module 11 is not provided.

Although in the embodiment described above, the component analysis with respect to the components having the feature quantity with respect to the near-infrared range is performed, by adopting a configuration in which the variable wavelength interference filter 5 is capable of dispersing the light in a range from the visible light range to the near-infrared range, the components having the feature quantity with respect to the visible light range can also be analyzed. Similarly, it is also possible to adopt a configuration in which the variable wavelength interference filter 5 is capable of also dispersing the light in the ultraviolet range, and in this case, it is possible to perform analysis of the component having the feature quantity with respect to the ultraviolet range, detection of a substance sensitive to the ultraviolet light, analysis of the distribution state of the substance, and so on.

Although there is adopted the configuration in which the variable wavelength interference filter 5 is provided with the electrostatic actuator 56 for varying the gap amount of the inter-reflecting film gap G1 in accordance with the voltage applied.

It is also possible to adopt a configuration of, for example, using a dielectric actuator disposing a first dielectric coil instead of the stationary electrode 561, and disposing a second dielectric coil or a permanent magnet instead of the movable electrode 562.

Further, it is also possible to adopt a configuration of using a piezoelectric actuator instead of the electrostatic actuator 56. In this case, for example, a lower electrode layer, a piezoelectric film, and an upper electrode layer are disposed on the holding section 522 in a stacked manner, and the voltage applied between the lower electrode layer and the upper electrode layer is varied as an input value, and thus the piezoelectric film is expanded or contracted to thereby make it possible to deflect the holding section 522.

In the embodiment described above, the temperature sensor 15 is provided, and the correction unit 183 corrects the wavelength, at which the feature quantity of the component of the analysis target can be obtained, based on the temperature thus detected to thereby obtain the measurement target wavelength.

In contrast, it is also possible to adopt a configuration in which, for example, the temperature sensor 15 is not provided. Also in this case, with respect to the components with small variation in absorption spectrum by the temperature, the component analysis with small error can be performed.

Although in the embodiment described above, there is described the example in which the variable wavelength interference filter 5 is used as the spectroscopic element, the AOTF or the LCTF can also be used. Further, the invention is not limited to the spectroscopic element capable of performing the integral-field spectroscopy, but it is also possible to use a spectroscopic element for performing only the spectroscopy with respect to a predetermined point. In this case, for example, the light transmitted through the spectroscopic measurement point for dispersing the incident light in the spectroscopic element enters the pixel opposed to the spectroscopic measurement point among the pixels constituting the imaging element, and the light intensity at the pixel is detected. Therefore, by, for example, translating the spectroscopic element to thereby translate the spectroscopic measurement point, the light intensity with respect to each of the pixels can be detected, and thus, it becomes possible to obtain the spectral image from the light intensity of each of the pixels.

Although in the embodiment described above, there is described the example in which the component analysis unit 185 calculates the calorie of the food, it is also possible to adopt a configuration of not performing the calculation of the calorie.

Besides the above, specific structure to be adopted when putting the invention into practice can arbitrarily be replaced with other structures and so on within the range in which the advantages of the invention can be achieved.

The entire disclosure of Japanese Patent Application No. 2012-284469 filed on Dec. 27, 2012 is expressly incorporated by reference herein.

What is claimed is:

1. A food analysis device adapted to detect a plurality of components included in a food, comprising:
    a spectroscopic element adapted to disperse light reflected by the food into a plurality of lights with respective wavelengths;
    an imaging element adapted to image the lights with the respective wavelengths obtained by the dispersion to obtain spectral images corresponding respectively to the wavelengths; and
    a processing section adapted to (i) obtain a spectrum of each pixel of the spectral images corresponding respectively to the wavelengths, (ii) detect which of the pixels of the spectral images are food-containing pixels by detecting which pixels include an absorption spectrum of water, and (iii) then detect, in the food-containing pixels, the plurality of components.

2. The food analysis device according to claim 1, wherein the spectroscopic element performs integral-field spectroscopy on the light reflected by the food, and the imaging element receives the light obtained by the integral-field spectroscopy using the spectroscopic element by each of the pixels independent of each other to obtain the spectral image constituted by the plurality of pixels.

3. The food analysis device according to claim 1, wherein the spectroscopic element is a variable wavelength Fabry-Perot etalon element.

4. The food analysis device according to claim 1, wherein the processing section calculates calorie of the food based on the plurality of components detected.

5. A method of detecting a plurality of components included in a food, the method comprising the steps of:
dispersing light reflected by the food into a plurality of lights with respective wavelengths;
imaging the lights with the respective wavelengths obtained by the dispersion to obtain spectral images corresponding respectively to the wavelengths;
obtaining a spectrum of each pixel of the spectral images corresponding respectively to the wavelengths;
detecting which of the pixels of the spectral images are food-containing pixels by detecting which pixels include an absorption spectrum of water; and
detecting, in the detected food-containing pixels, the plurality of components.

* * * * *